United States Patent [19]
Dykstra

[11] 4,139,010
[45] Feb. 13, 1979

[54] STERILITY GUARD FOR PIERCING DEVICES, CONNECTORS AND NEEDLES

[75] Inventor: Edward G. Dykstra, East Aurora, N.Y.

[73] Assignee: Ethox Corporation, Buffalo, N.Y.

[21] Appl. No.: 852,478

[22] Filed: Nov. 17, 1977

[51] Int. Cl.$^2$ ............................................... A61M 5/00
[52] U.S. Cl. ................................... 128/221; 128/247; 128/218 S; 285/3
[58] Field of Search ................... 128/247, 221, 218 N, 128/218 S, 214 R, 214 D, 214 C, 214.2, 272.3, 348, 349 R; 285/3, 260; 206/571, 438

[56] References Cited
U.S. PATENT DOCUMENTS

| | | | |
|---|---|---|---|
| 3,987,791 | 10/1976 | Chittenden et al. | 128/272.3 |
| 4,004,586 | 1/1977 | Christensen et al. | 128/214 D |
| 4,056,116 | 11/1977 | Carter et al. | 128/247 X |
| 4,059,112 | 11/1977 | Tischlinger | 128/221 X |

FOREIGN PATENT DOCUMENTS 2402310  7/1974  Fed. Rep. of Germany ........ 128/272.3

*Primary Examiner*—John D. Yasko
*Attorney, Agent, or Firm*—Christel & Bean

[57] ABSTRACT

A sterility guard for piercing devices, connectors and needles such as are used in the medical and surgical fields, which gives positive indication if the same has been removed from the piercing device or other connector and subsequently replaced, thereby compromising the sterility of the device.

In one form a tubular guard closed at one end is adapted to be applied over a blood spike, for instance, and a projecting portion at the open end of the guard is provided with an integral extension which is engageable in an opening in a portion of the blood spike or a connector of another kind. This extension has a weakened or attenuated portion which is broken when the guard is removed to give a positive indication that the guard may have been removed even though it is later replaced.

In another form the guard is used to protect the sterility of the otherwise exposed ends of a pair of connectors or the like. In this form the guard itself may comprise a tubular member open at both ends and an extension such as referred to in the preceding paragraph will be provided at each end of the tubular guard, one of the extension being connected with each of the connector portions which is being protected by the guard.

8 Claims, 7 Drawing Figures

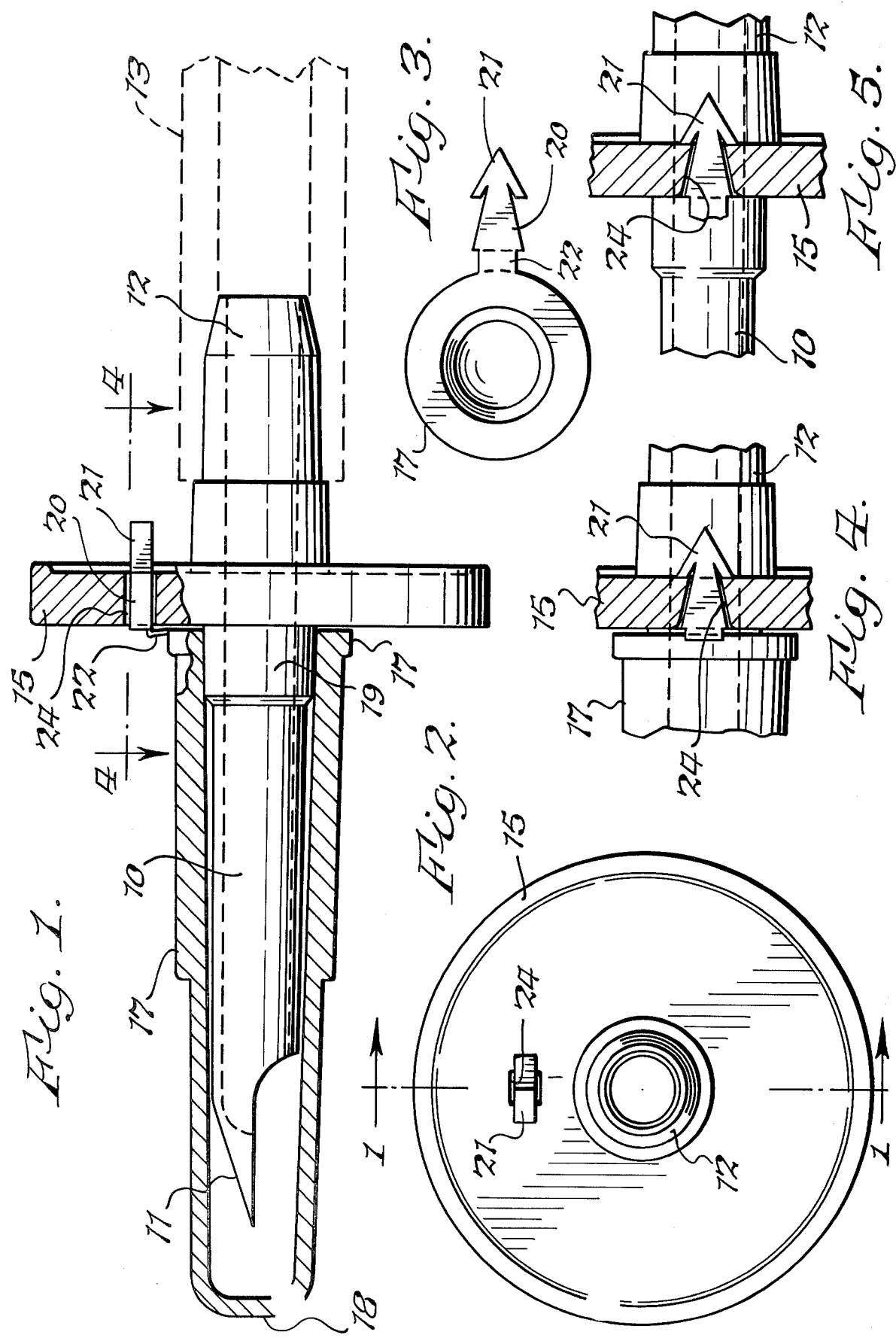

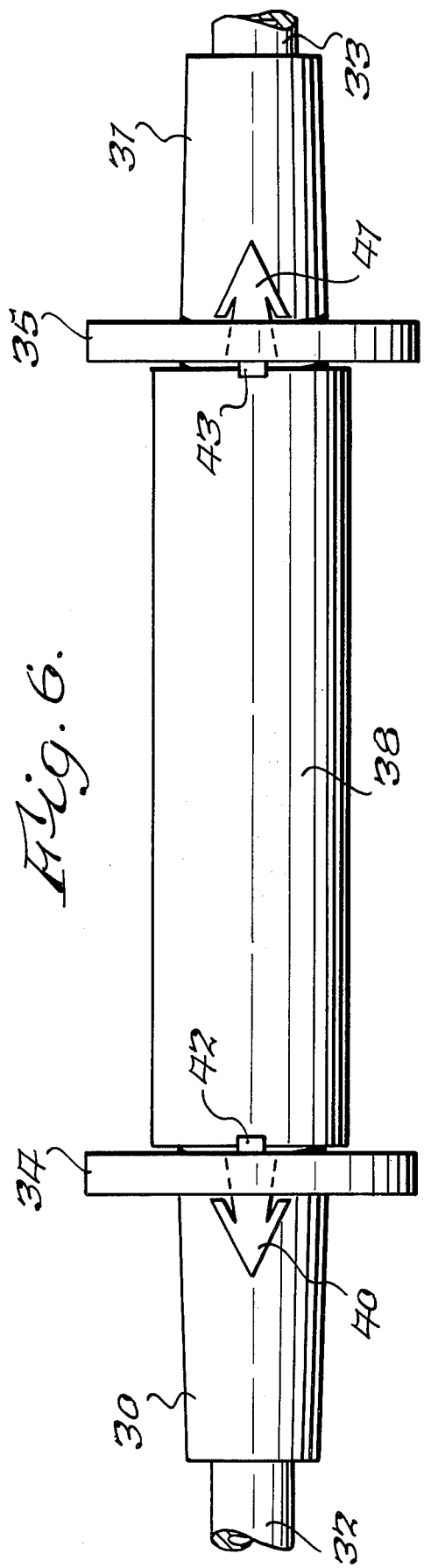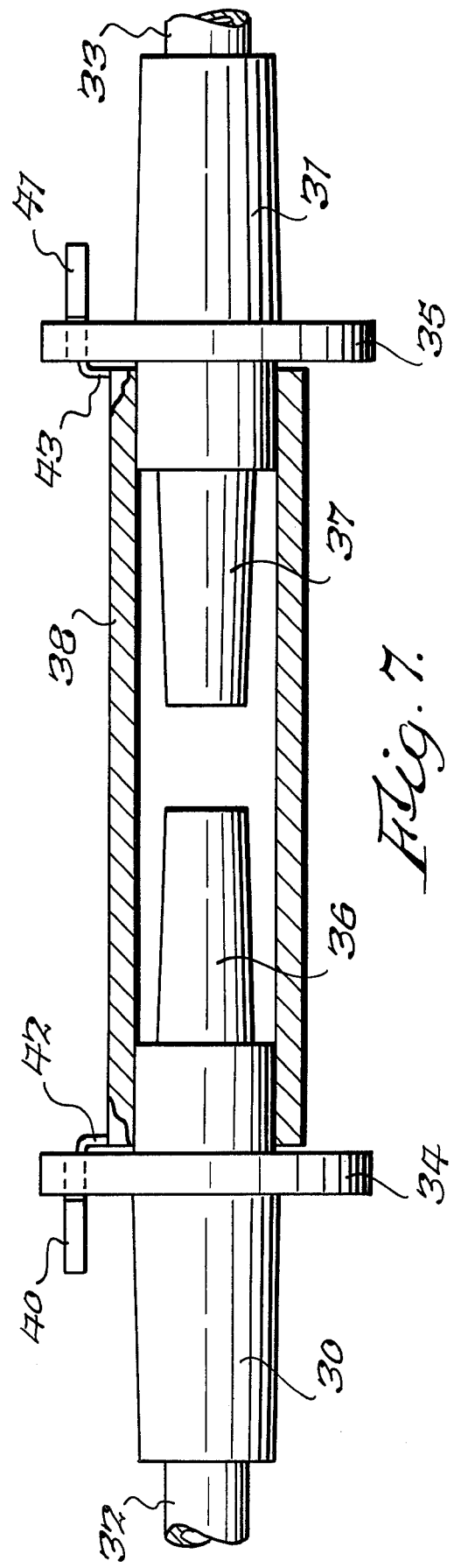

STERILITY GUARD FOR PIERCING DEVICES, CONNECTORS AND NEEDLES

BACKGROUND OF THE INVENTION

This invention relates to a sterility guard for piercing devices or connectors such as are used in the medical and surgical fields and more particularly to a sterility guard which gives positive indication if the same has been removed from the piercing device or other connector and subsequently replaced.

In the prior art various caps or guards have been employed to protect the sterility of blood spikes or similar piercing devices and also connectors of various kinds. In some of these prior art proposals, if the sterility guard or other protective device is removed accidentally or for one reason or another, it may merely be replaced and there is no indication that the piercing device or a similar member has been exposed to contamination and may no longer be sterile.

In some prior art devices of this general type attempts have been made to protect the sterility of guards or connectors of the type here under consideration against the possibility of contamination by early removal and replacement of the guard. Some of these devices are in the form of adhesive tape wound about the joint between the guard and the piercing device or connector. Among others are shrink bands and heat seals between the guard and the device. All of these devices are awkward and are expensive and not foolproof in use and do not insure positively against undetectable replacement.

SUMMARY OF THE INVENTION

In the sterility guard of the present invention a tubular guard closed at one end is adapted to be applied over a blood spike, for instance, and a projecting portion at the open end of the guard is provided with an integral extension which is engageable in an opening in a portion of the blood spike or a connector of another kind. This extension has a weakened or attenuated portion which is broken when the guard is removed, thus giving a positive indication that the guard has been removed even though it is later replaced.

In instances where the guard is used to protect the sterility of the otherwise exposed ends of a pair of connectors or the like, the guard itself may comprise a tubular member open at both ends and in this instance the extension referred to in the preceding paragraph will be provided at both ends of the tubular guard, one of the extension being connected with each of the connector portions which is being protected by the guard.

The sterility guard of the present invention is also useful in cases where it is accidentally removed as by being knocked off or blown off by intense pressure in the device which it protects.

A further advantage of the sterility guard of the present invention resides in the fact that the portion of the guard which is broken off when the guard is removed remains in the opening in which it is engaged so that it will not fall out and possibly interfere with the procedure in which the device is being used.

BRIEF DESCRIPTION OF THE DRAWINGS

FIG. 1 is a longitudinal cross-sectional view through one form of the sterility guard device of the present invention applied to a blood spike;

FIG. 2 is an elevational view taken from the right-hand end of FIG. 1;

FIG. 3 is a right-hand end view of the guard of FIG. 1 shown before it is assembled on a blood spike or the like;

FIG. 4 is a fragmentary cross-sectional view on the line 4—4 of FIG. 1;

FIG. 5 is a view similar to FIG. 4 but showing the blood spike after the sterility guard has been removed therefrom;

FIG. 6 is an elevational view of a modified form of the sterility guard of the present invention designed to protect the otherwise exposed ends of a pair of connectors; and FIG. 7 is a longitudinal cross-sectional view of the embodiment of FIG. 6 viewed at right angles to FIG. 6.

DESCRIPTION OF THE ILLUSTRATED EMBODIMENT

In FIG. 1 the numeral 10 designates a conventional blood spike which has a piercing formation 11 at one end and a connecting nipple 12 at the other end for connecting with a tube or the like as shown in dotted lines at 13. Blood spikes and similar devices are commonly employed by piercing the same through the diaphragm of a plastic bag containing blood or through the rubber stopper of a glass container. Similar piercing devices are employed for connecting with intravenous solution containers and for other related purposes. An intermediate flange formation 15 is conventionally employed to protect the piercing portion of the blood spike from contact with the hand of the operator which normally grips the blood spike and connected tube at the right-hand portion of the blood spike as viewed in FIG. 1. Flange 15 also serves as a surface for the operator to push against to insert the spike or other device.

The sterility guard of the present invention which is illustrated in FIGS. 1 through 5 comprises a tubular body portion 17 of elastomeric plastic material having a closed outer end 18 and an open end portion which fits tightly over a cylindrical portion 19 of blood spike 10.

As shown in FIG. 3, the open end of the tubular portion 17 of the sterility guard of the present invention is molded with a laterally projecting portion 20 having an arrowhead shaped outer portion 21 and a connecting portion 22 of attenuated thickness which connected the member 20 with the tubular body portion 17 of the sterility guard. The flange 15 is provided with a rectangular opening 24 which has tapered end walls as shown in FIGS. 4 and 5.

In applying the sterility guard 17 to the blood spike 10 the laterally extending portion 20 is bent downwardly at right angles as clearly shown in FIG. 1 and projected through the opening 24 in flange 15. During this insertion the arrowhead portions 21 compresses laterally as it passes through opening 24 and then expands laterally to the position shown in FIG. 4. Following assembly in this matter it is not possible to remove the guard 17 from the blood spike 10 excepting by rupturing the attenuated or weakened portion 22 which is a clear indication that the sterility guard has been removed, even though the guard is later replaced.

Provision is made so that when the guard 17 is removed, the protective tamper-proof seal portion 20 including the arrowhead 21 is retained in the opening 24 so that it does not clutter up the work area or the like. Thus, as clearly shown in FIG. 5, the torn-off portion 20 remains in the opening 24 due to the tapering formation of the portion 20 and the tapering of the opening 24 in flange 15 in cooperation with the arrowhead portion 21.

It is to be understood that the guard and the tamper-proof provision disclosed herein may be employed in other uses analogous to that of the blood spike 10. For instance, the element 10 may be a mere connecting tube to be inserted in the end of a catheter. Otherwise the cooperation between the portion 20 of the guard 17 and the flange 15 of the connector may be the same as described herein in connection with the blood spike.

FIGS. 6 and 7 illustrate an embodiment of the principles of the present invention where it is desired to protect the sterility of a pair of connectors. These connectors may be used for a variety of purposes such as, for instance, to insert a length of tubing between the connectors, to connect them to a Y or for connecting them with other pieces of medical equipment.

In FIGS. 6 and 7 a pair of adaptors or connectors 30 and 31 each is fixed to the end of a flexible tubing as at 32 and 33 respectively. Each of the adaptors 30 and 31 is provided with a flange as at 34 and 35, respectively, and these flanges have openings therein corresponding to the opening 24 of flange 15 of the previous embodiment for receiving the tamper-proof guard element of the present invention. In one form of the present embodiment the adaptors 30 and 31 have nipple portions 36 and 37 for connecting with tubing or other medical equipment.

In this embodiment the guard member comprises a tubular body 38 which is open at both ends and fits securely over the facing ends of the adaptors 30 and 31 as shown in FIG. 7. In the present embodiment each end of the guard 38 has extending laterally therefrom an arrow-shaped portion 40 and 41 which in its initial molded condition extends radially outwardly as shown in FIG. 3 of the previous embodiment. The arrow-shaped portions 40 and 41 have attenuated frangible portions 42 and 43, likewise corresponding to the portion 22 of FIG. 3 of the previous embodiment.

Preferred embodiments of the present invention have been described herein and illustrated in the accompanying drawings by way of example. However, it is to be understood that numerous modifications may be made without departing from the broad spirit and scope of the invention as defined in the appended claims.

I claim:

1. In combination, a tubular member for medical use and a tubular guard for enclosing an end portion of said tubular member to maintain sterility thereof, said guard being adapted to telescope over said member, said member having a portion projecting radially therefrom and having an opening therein, said guard having a portion projecting from the end thereof adjacent to said radially projecting portion, the projecting portion of said guard being of elastomeric material and having a head portion larger than said opening adapted to be forced through said opening by compression of said head portion and expand after passage through said opening to prevent withdrawal thereof, said guard projecting portion having a frangible neck portion adapted to rupture when said guard is forcibly removed from said tubular member and thus signal the fact that the guard has been removed from the tubular member.

2. A combination according to claim 1 wherein the head portion of said projecting portion is of generally triangular form with one angle thereof projecting outwardly to facilitate entry thereof into said opening and the other two angles adapted to engage securely at the exit side of said opening after passage of said head portion through said opening.

3. A combination according to claim 1 wherein said tubular member comprises a piercing formation at one end thereof and a connector at its opposite end with said radially projecting portion disposed between said piercing formation and said connector.

4. A combination according to claim 3 wherein said tubular guard is closed at the end opposite to said projecting portion thereof to enclose said piercing formation.

5. A combination according to claim 2 wherein said tubular member comprises a piercing formation at one end thereof and a connector at its opposite end with said radially projecting portion disposed between said piercing formation and said connector.

6. A combination according to claim 1 wherein said frangible neck portion is substantially thinner than said head portion to provide a hinge and to facilitate rupture thereof upon removal of said guard.

7. A combination according to claim 1 including a pair of said tubular members to serve as connectors to medical equipment and wherein said tubular guard telescopes over adjacent ends of said pair of tubular members to maintain sterility of said tubular member ends, each of said tubular members having a portion projecting radially therefrom and having an opening therein, said tubular guard having a portion projecting therefrom at each end thereof, each such portion having a head portion larger than said opening and adapted to be forced through said openings to prevent withdrawal therefrom, each of said guard projecting portions having a frangible neck portion connecting the same to said tubular guard.

8. A combination according to claim 1 wherein said opening in the radially projecting portion of said tubular member is smaller at the exit end thereof than at its entry end, the medical portion of the projecting portion of said guard being correspondingly tapered so that when the neck portion is ruptured the outer projecting portion of said guard is retained in said opening.

* * * * *